United States Patent
Lee et al.

(10) Patent No.: US 10,466,323 B2
(45) Date of Patent: Nov. 5, 2019

(54) MAGNETIC RESONANCE IMAGING APPARATUS AND METHOD

(71) Applicant: SAMSUNG ELECTRONICS CO., LTD., Suwon-si (KR)

(72) Inventors: Dae-ho Lee, Seongnam-si (KR); Jae-moon Jo, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 206 days.

(21) Appl. No.: 15/520,230

(22) PCT Filed: Aug. 28, 2015

(86) PCT No.: PCT/KR2015/009057
§ 371 (c)(1),
(2) Date: Apr. 19, 2017

(87) PCT Pub. No.: WO2016/072604
PCT Pub. Date: May 12, 2016

(65) Prior Publication Data
US 2017/0315191 A1  Nov. 2, 2017

(30) Foreign Application Priority Data

Nov. 3, 2014 (KR) .......................... 10-2014-0151218

(51) Int. Cl.
*G01R 33/48* (2006.01)
*A61B 5/055* (2006.01)
(Continued)

(52) U.S. Cl.
CPC .......... *G01R 33/4818* (2013.01); *A61B 5/055* (2013.01); *G01R 33/3621* (2013.01);
(Continued)

(58) Field of Classification Search
CPC ............ G01R 33/4818; G01R 33/3621; G01R 33/5611; G01R 33/56509; G01R 33/567;
(Continued)

(56) References Cited

U.S. PATENT DOCUMENTS 5,657,758 A * 8/1997 Posse ................. G01R 33/4833
324/307
5,709,208 A * 1/1998 Posse ................. G01R 33/4833
324/307
(Continued)

FOREIGN PATENT DOCUMENTS

JP 2011-143241 A 7/2011
KR 10-2010-0081005 A 7/2010

OTHER PUBLICATIONS

Communication dated Jan. 5, 2016, issued by the Korean Intellectual Property Office in counterpart Korean Patent Application No. 10-2014-0151218.
(Continued)

*Primary Examiner* — Dixomara Vargas
(74) *Attorney, Agent, or Firm* — Sughrue Mion, PLLC

(57) ABSTRACT

A magnetic resonance imaging (MRI) apparatus includes a radio frequency (RF) receiver which acquires a magnetic resonance (MR) signal received by at least one channel coil, and an image processor which acquires a data set of a k-space for the at least one channel coil by oversampling the MR signal in a readout direction of the k-space, divides the data set into a plurality of sub-data sets, and acquires an MR image based on the plurality of sub-data sets.

20 Claims, 12 Drawing Sheets

(51) Int. Cl.
*G01R 33/36* (2006.01)
*G01R 33/561* (2006.01)
*G01R 33/565* (2006.01)
*G01R 33/567* (2006.01)
*A61B 5/11* (2006.01)

(52) U.S. Cl.
CPC ....... *G01R 33/482* (2013.01); *G01R 33/4824* (2013.01); *G01R 33/567* (2013.01); *G01R 33/5611* (2013.01); *G01R 33/56509* (2013.01); *A61B 5/1128* (2013.01)

(58) Field of Classification Search
CPC .... G01R 33/482; G01R 33/4824; A61B 5/055
See application file for complete search history.

(56) References Cited

U.S. PATENT DOCUMENTS

| | | | |
|---|---|---|---|
| 5,879,299 A * | 3/1999 | Posse | G01R 33/4833 324/307 |
| 6,943,548 B1 | 9/2005 | Hertz | |
| 7,382,127 B2 | 6/2008 | Gaddipati et al. | |
| 8,232,800 B2 | 7/2012 | Park et al. | |
| 8,710,838 B2 | 4/2014 | Miyazaki et al. | |
| 2006/0247515 A1 | 11/2006 | Moriguchi et al. | |
| 2006/0264735 A1 | 11/2006 | Stemmer | |
| 2008/0021304 A1 | 1/2008 | Stemmer | |
| 2008/0303521 A1 | 12/2008 | Beatty et al. | |
| 2010/0272337 A1 | 10/2010 | Shirai et al. | |
| 2014/0203804 A1 | 7/2014 | Duensing | |

OTHER PUBLICATIONS

Search Report dated Dec. 7, 2015, issued by the International Searching Authority in counterpart International Patent Application No. PCT/KR2015/009057 (PCT/ISA/220, PCT/ISA/210).
Written Opinion dated Dec. 7, 2015, issued by the International Searching Authority in counterpart International Patent Application No. PCT/KR2015/009057 (PCT/ISA/237).
Communication dated Nov. 8, 2017, issued by the European Patent Office in counterpart European Application No. 15857284.2.
Stab, et al., "Applying Parallel Imaging for SNR Enhancement", Apr. 17, and May 1-7, 2010, Proceedings of the International Society for Magnetic Resonance in Medicine, XP040614313, 1 page total.
Haacke, et al., "Oversampling to Avoid Aliasing" in "Magnetic Resonance Imaging: Physical Principles and Sequence Design", Jan. 1, 1999, XP055420205, p. 343.
Bilgic, et al., "Wave-CAIPI for Highly Accelerated 3D Imaging", Jul. 1, 2014, Magnetic Resonance in Medicine, vol. 73, No. 6, XP55349786, pp. 2152-2162.

* cited by examiner

[Fig. 1]
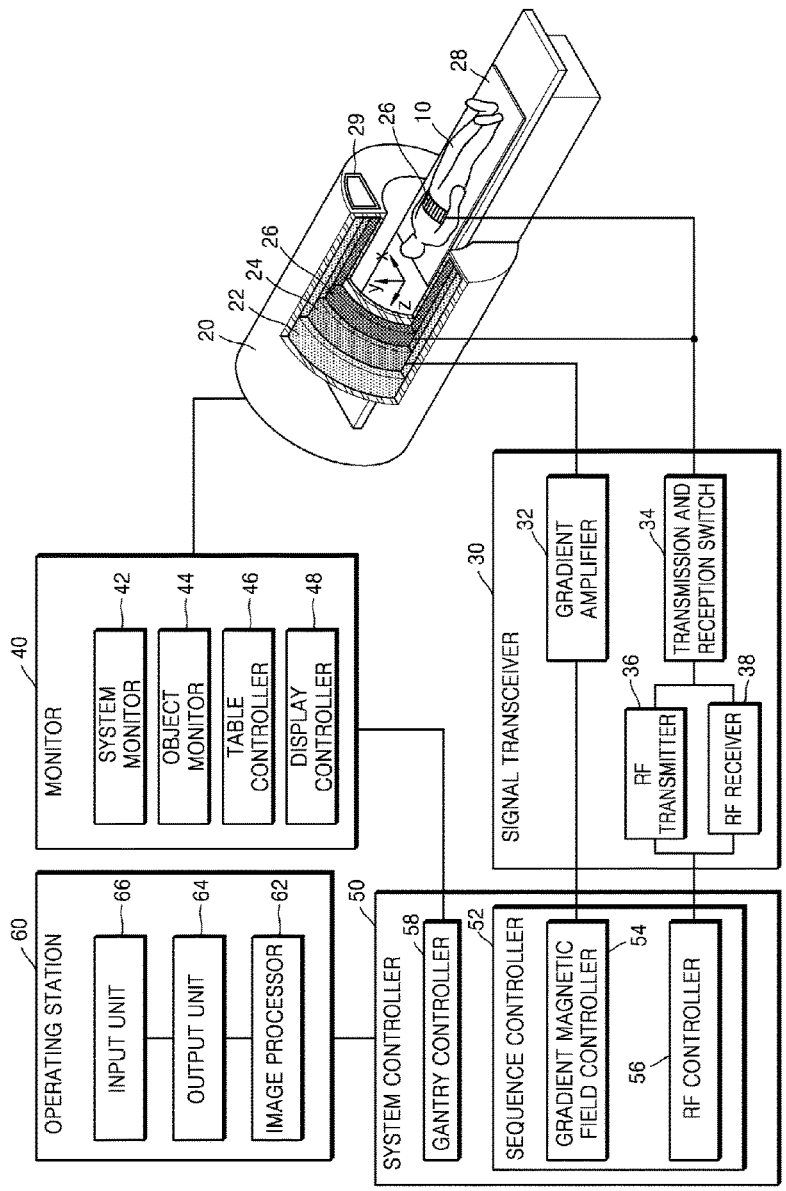
[Fig. 2]
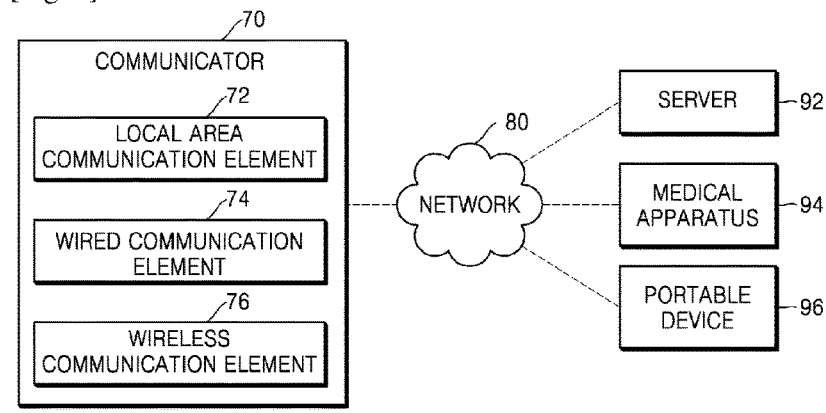

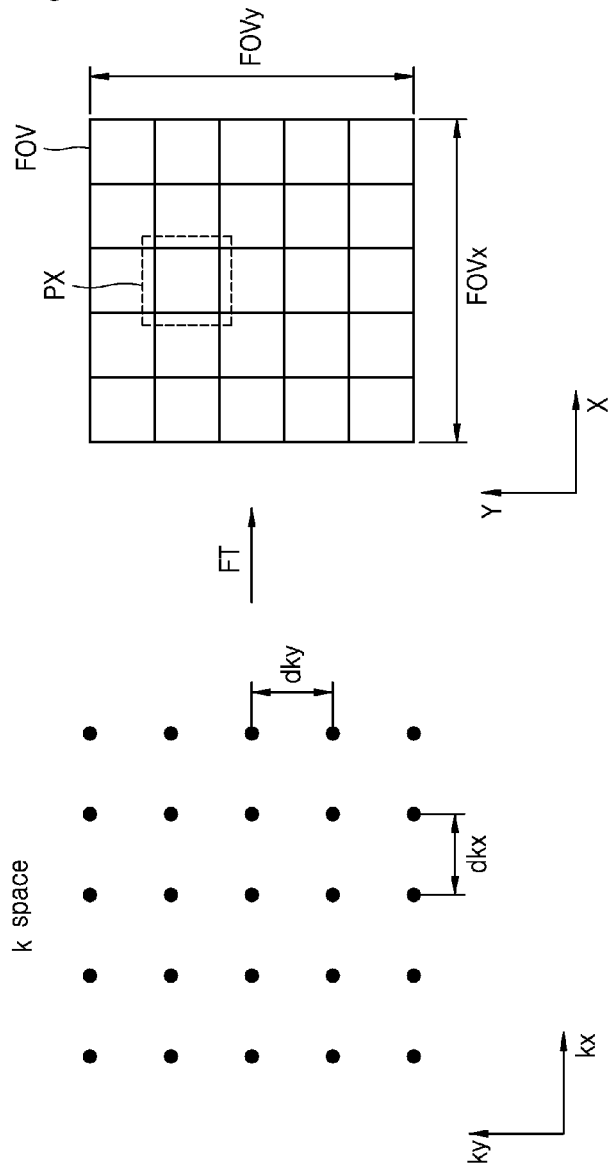
[Fig. 3]

[Fig. 4]
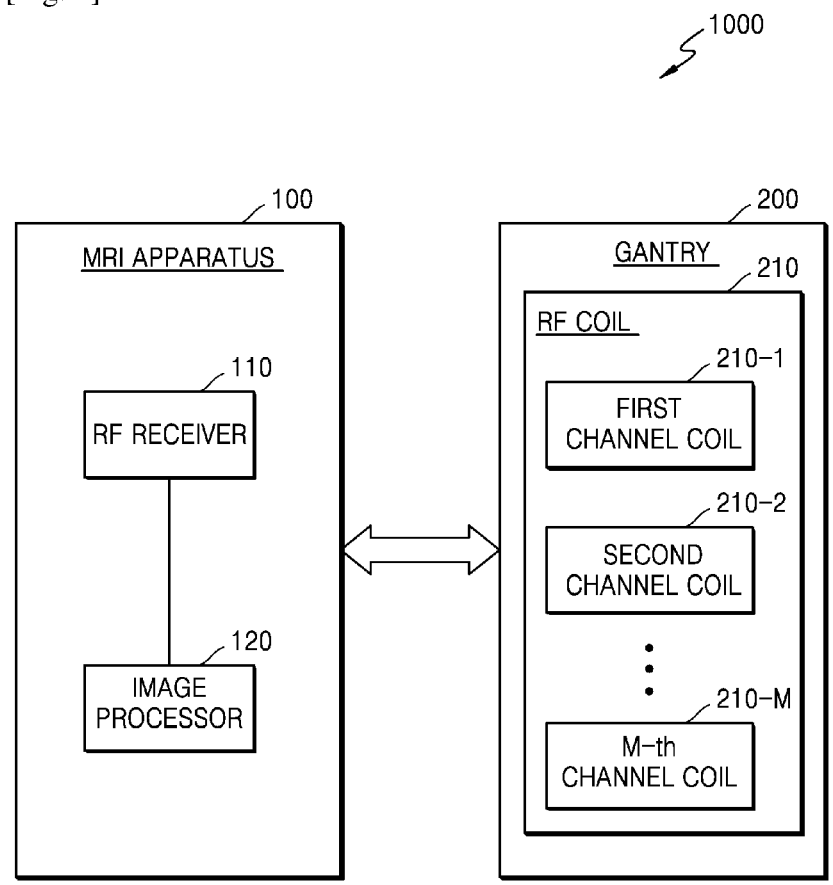
[Fig. 5]
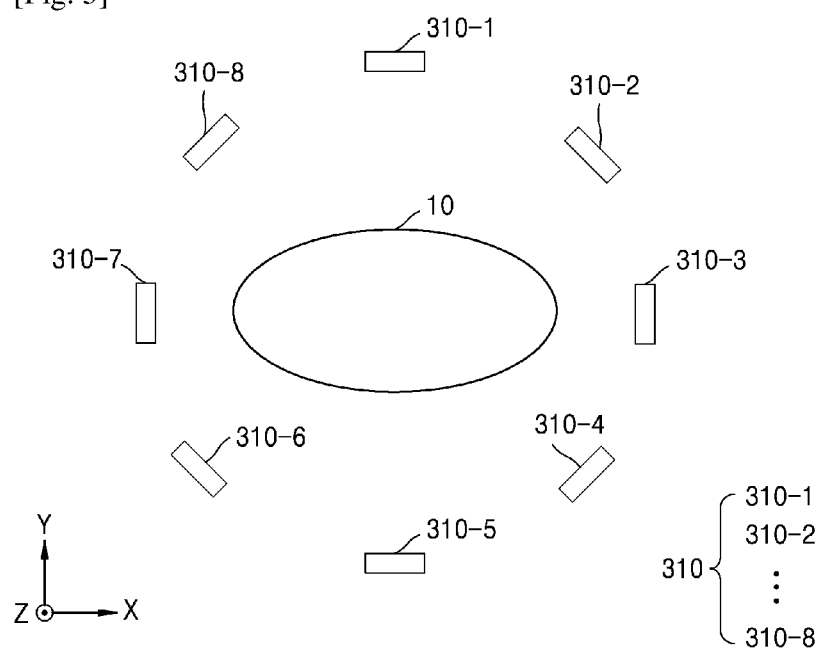

[Fig. 6a]
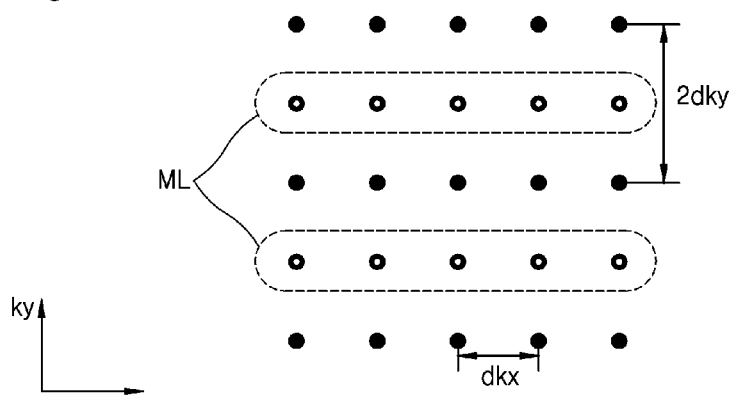
[Fig. 6b]
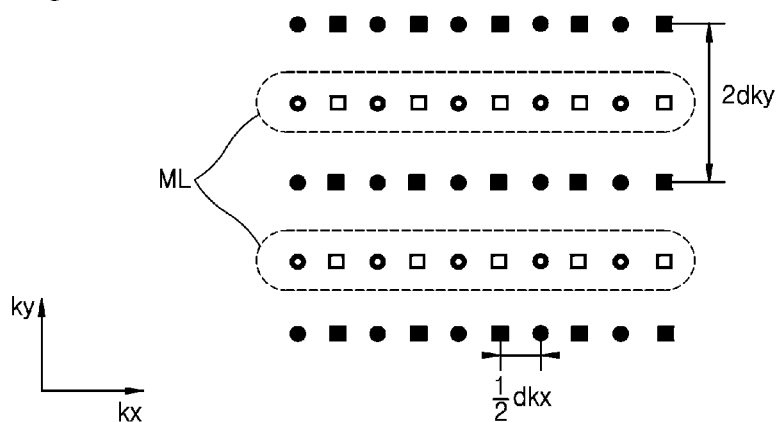

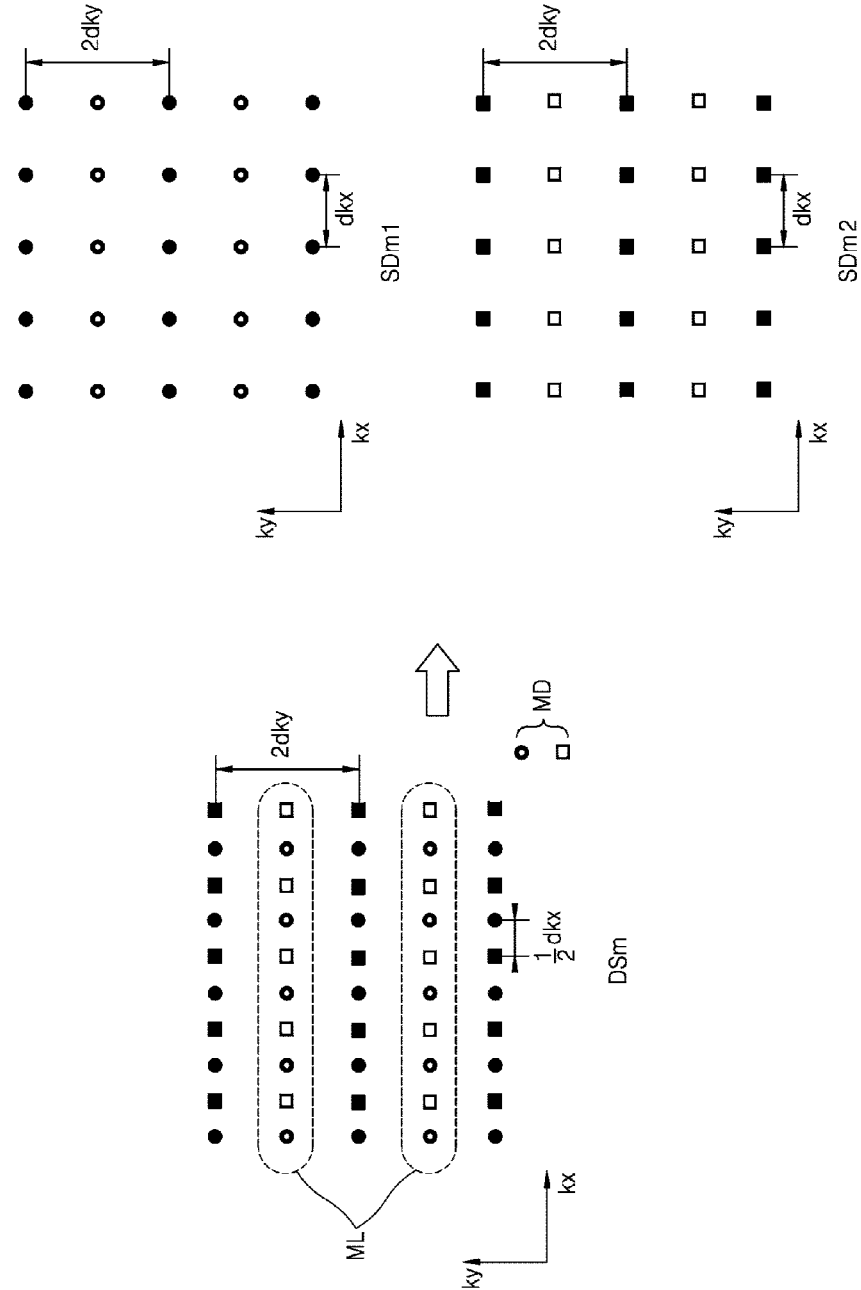
[Fig. 7]

[Fig. 8]
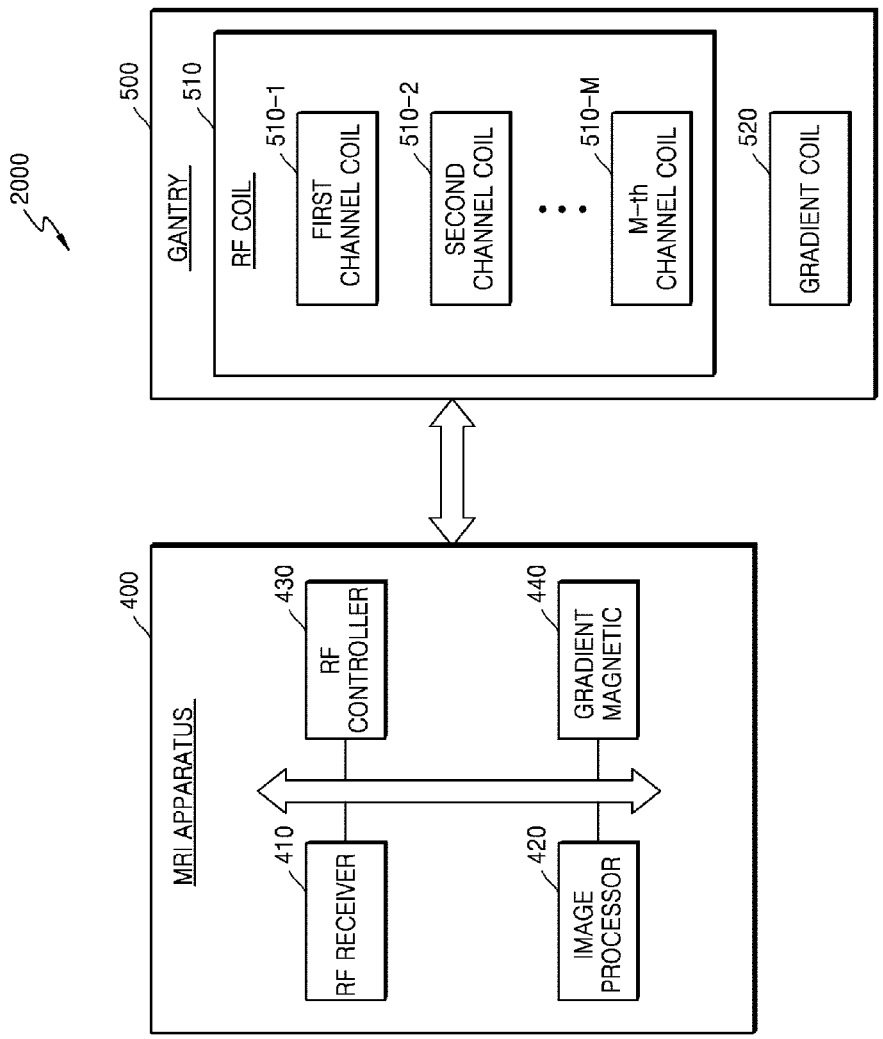
[Fig. 9]
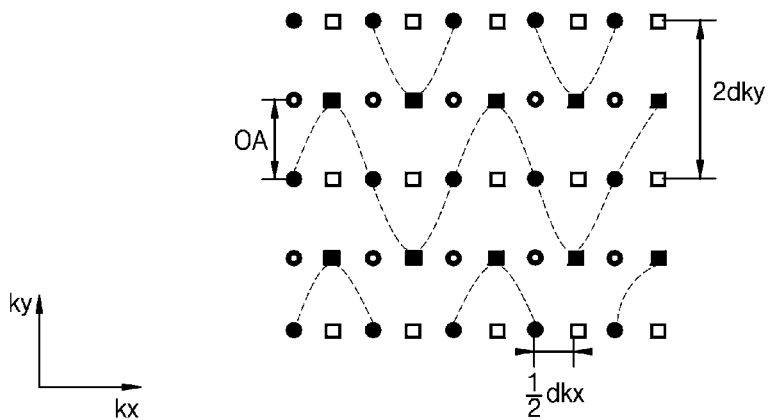

[Fig. 10a]
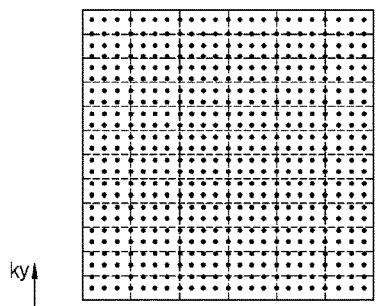
[Fig. 10b]
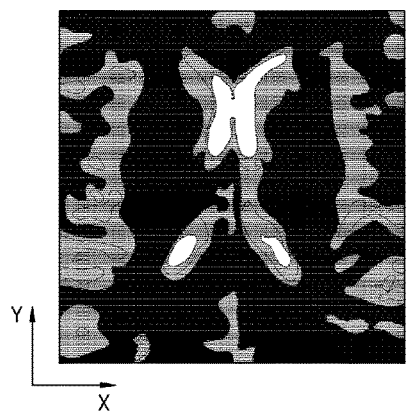
[Fig. 10c]
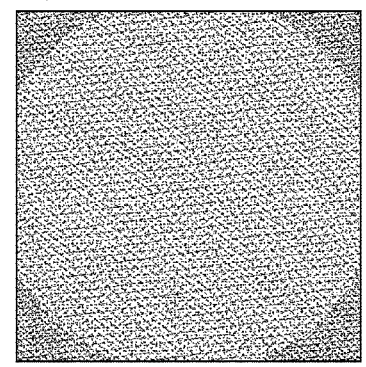
[Fig. 11a]
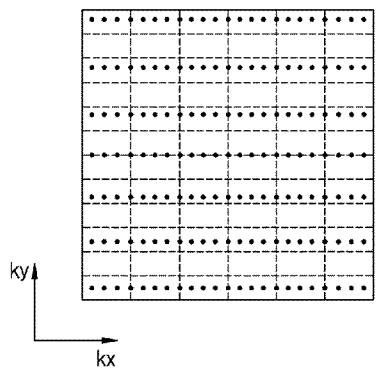

[Fig. 11b]
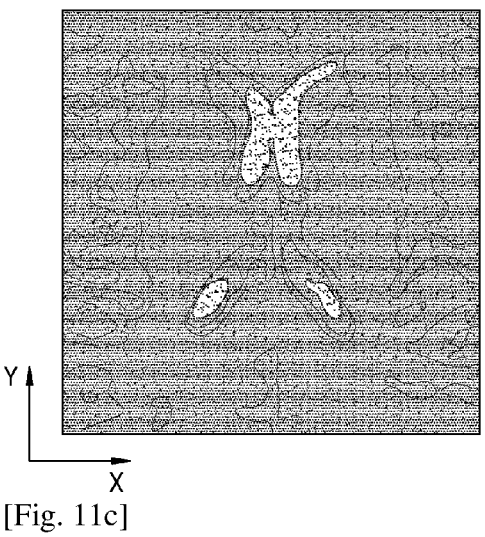
[Fig. 11c]
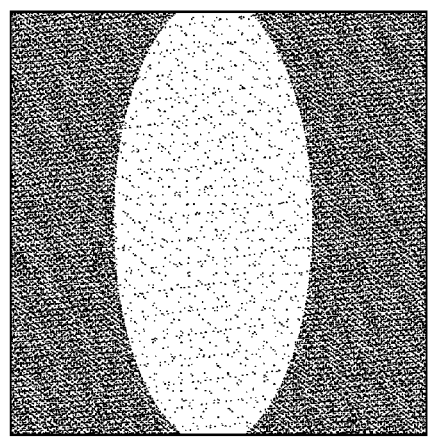
[Fig. 12a]
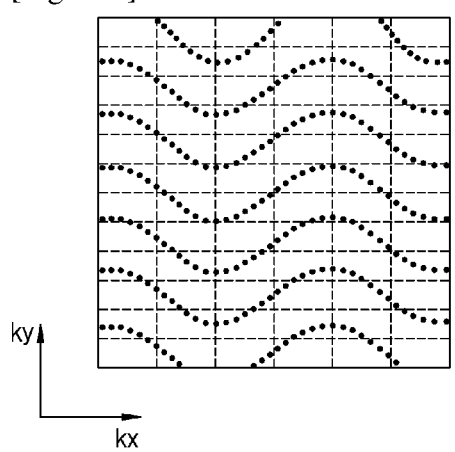

[Fig. 12b]
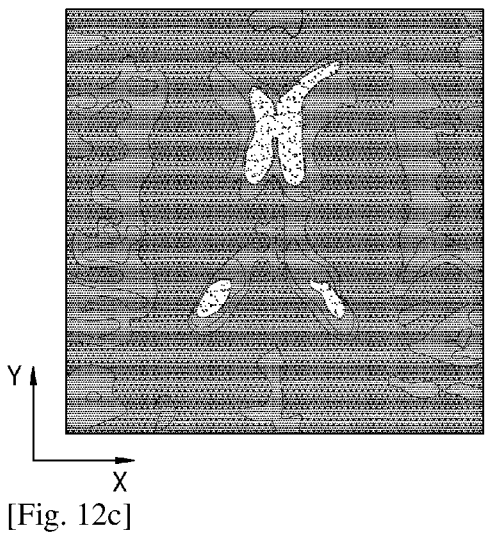
[Fig. 12c]
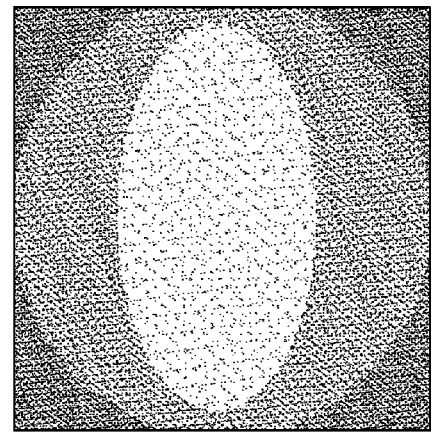
[Fig. 13a]
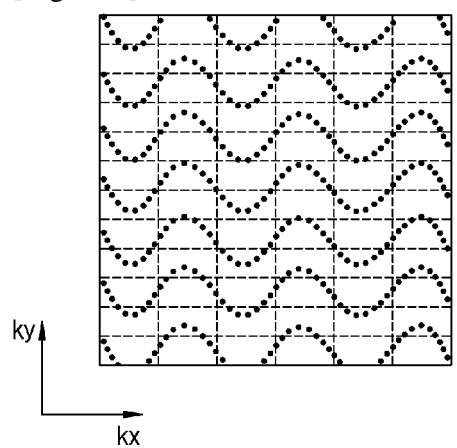

[Fig. 13b]
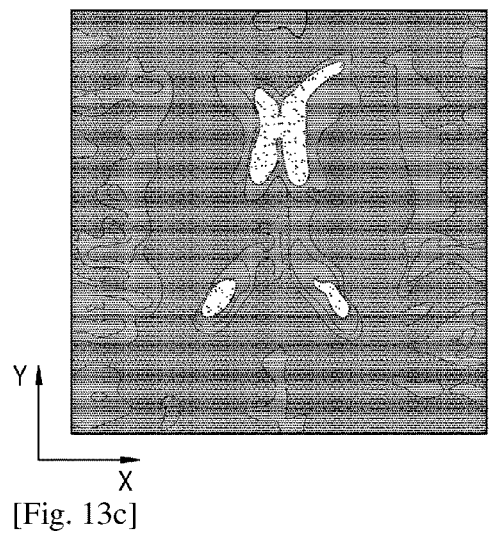
[Fig. 13c]
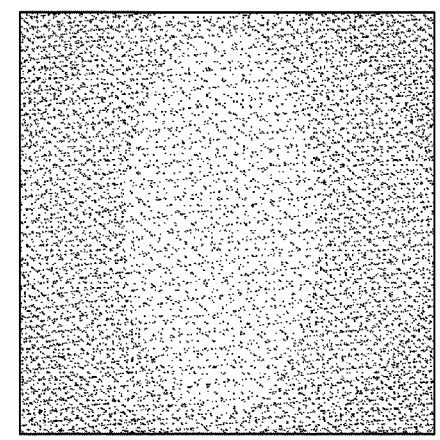
[Fig. 14a]
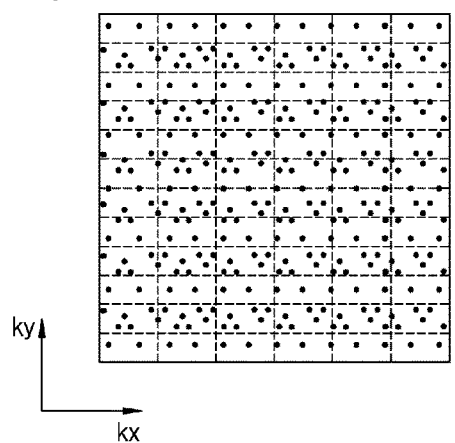

[Fig. 14b]
[Fig. 14c]
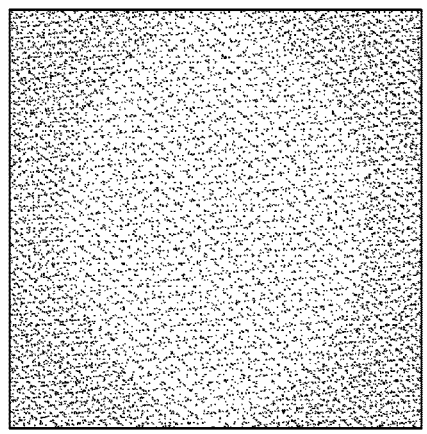
[Fig. 15a]
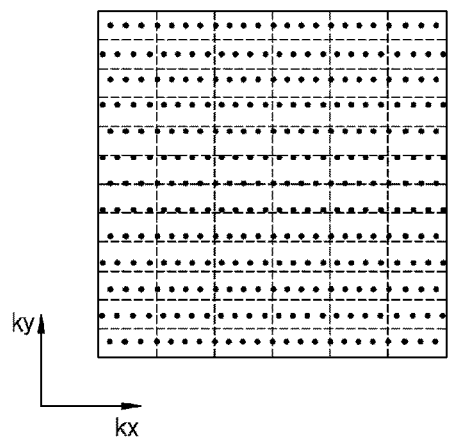

[Fig. 15b]
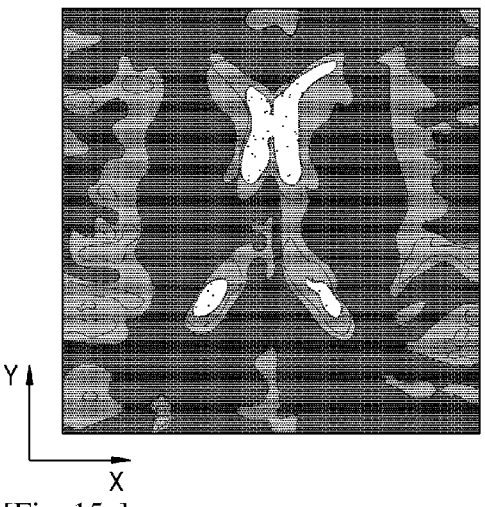
[Fig. 15c]
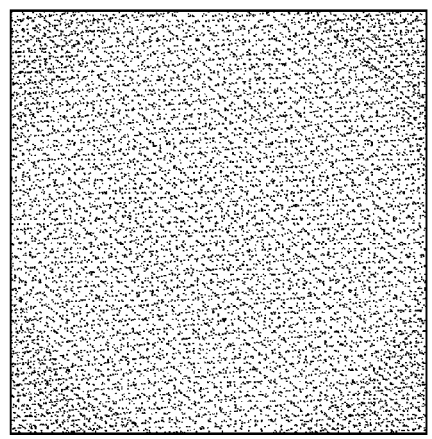
[Fig. 16]
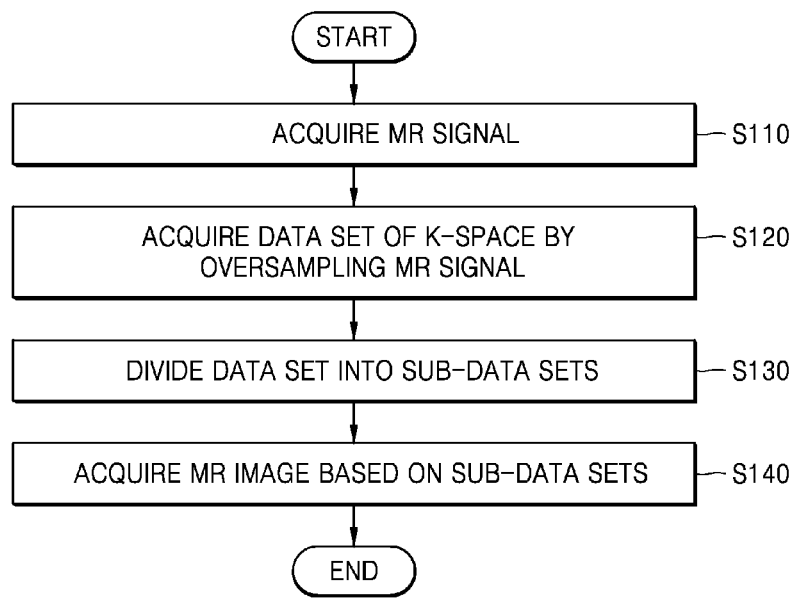

MAGNETIC RESONANCE IMAGING APPARATUS AND METHOD

TECHNICAL FIELD

One or more exemplary embodiments relate to magnetic resonance imaging (MRI) apparatuses and methods, and more particularly, to MRI apparatuses and methods, in which the quality of magnetic resonance images is improved.

BACKGROUND ART

Magnetic resonance imaging (MRI) apparatuses photograph a subject by using a magnetic field, and are widely used for accurate diagnosis of diseases since the MRI apparatuses three-dimensionally show not only bones, but also discs, joints, nerves, and ligaments at a desired angle. A magnetic resonance (MR) image may be obtained by sampling an MR signal to obtain digital data in k-space and generating image data based on the obtained digital data.

Recently, research is being conducted into a method for improving quality of an MR image without increasing a time taken to acquire the MR image.

DISCLOSURE

Technical Solution

According to one or more embodiments, a magnetic resonance imaging (MRI) apparatus includes a radio frequency (RF) receiver which acquires a MR signal received by at least one channel coil; and an image processor which acquires a data set of a k-space for the at least one channel coil by oversampling the MR signal in a readout direction of the k-space, divides the data set into a plurality of sub-data sets, and acquires an MR image based on the plurality of sub-data sets.

Advantageous Effects

One or more exemplary embodiments include apparatuses and methods for processing magnetic resonance (MR) images, in which the quality of MR images is improved.

DESCRIPTION OF DRAWINGS

These and/or other aspects will become apparent and more readily appreciated from the following description of the embodiments, taken in conjunction with the accompanying drawings in which:

FIG. 1 is a block diagram of a general MRI system;

FIG. 2 is a schematic diagram illustrating a structure of a communicator;

FIG. 3 illustrates a data set of k-space and a field of view (FOV) of a magnetic resonance (MR) image;

FIG. 4 is a block diagram of an MRI system including an MRI apparatus, according to an embodiment;

FIG. 5 illustrates an RF coil included in an MRI system according to an embodiment;

FIGS. 6A and 6B illustrate data sets in k-space;

FIG. 7 illustrates an example in which an image processor according to an embodiment divides a data set acquired via oversampling into a plurality of sub-data sets;

FIG. 8 is a block diagram of an MRI system according to an embodiment;

FIG. 9 illustrates an example of a data set in k-space that is acquired by an image processor according to an embodiment;

FIGS. 10A-10C illustrate a simulation performed where MR image is acquire based on data set of k-space via full sampling using numerical phantom.

FIGS. 11A-11C illustrate a simulation performed where MR image is acquire based on data set of k-space via undersampling an using numerical phantom.

FIGS. 12A-12C illustrate a simulation performed where MR image is acquire based on data set of k-space via oversampling in a readout direction using numerical phantom.

FIGS. 13A-13C illustrate a simulation performed with acceleration factors RP in phase directions Ky of the data sets, and increase of the image quality.

FIGS. 14A-14C illustrate another simulation performed where MR image is acquire.

FIGS. 15A-15C illustrate a simulation performed with maximum cycle of oscillation.

FIG. 16 is a flowchart of an MRI processing method according to an embodiment.

BEST MODE

According to one or more embodiments, a magnetic resonance imaging (MRI) apparatus includes a radio frequency (RF) receiver which acquires a MR signal received by at least one channel coil; and an image processor which acquires a data set of a k-space for the at least one channel coil by oversampling the MR signal in a readout direction of the k-space, divides the data set into a plurality of sub-data sets, and acquires an MR image based on the plurality of sub-data sets.

The image processor may undersample the MR signal in a phase direction of the k-space.

The image processor may acquire the MR image based on the plurality of sub-data sets via parallel imaging.

The image processor may acquire a plurality of channel coil images for a plurality of virtual channel coils respectively having virtual sensitivities, based on the plurality of sub-data sets, and acquire the MR image by synthesizing the plurality of channel coil images based on a sampling pattern of the k-space and the virtual sensitivities.

The image processor may acquire a plurality of corrected sub-data sets by estimating missing data that is data not acquired in each of the plurality of sub-data sets, and acquire the MR image based on the plurality of corrected sub-data sets.

The image processor may estimate the missing data in each of the plurality of sub-data sets, based on calibration data that is acquired via calibration.

The image processor may acquire the calibration data from a portion of the data set or acquire the calibration data independently of the data set.

The image processor may oversample the MR signal at a sampling rate that is higher than a Nyquist rate that is determined based on a field of view (FOV) of the MR image.

The data set acquired by the image processor may include an oscillated sampling pattern in a phase direction of the k-space.

The MRI apparatus further includes a gradient coil controller which modulates a gradient magnetic field that is generated by a gradient coil. The image processor may acquire the data set having the oscillated sampling pattern by arranging digital data acquired by oversampling the MR signal in the k-space based on the modulated gradient magnetic field.

According to one or more embodiments, an MRI system includes at least one RF channel coil which receives a MR signal emitted from an object; an RF receiver which acquires the MR signal; and an image processor which acquires a data set of a k-space for the at least one RF channel coil by oversampling the MR signal in a readout direction of the k-space, divides the data set into a plurality of sub-data sets, and acquires an MR image based on the plurality of sub-data sets.

The image processor may oversample the MR signal, and undersample the MR signal in a phase direction of the k-space.

The MRI system further includes a gradient coil which generates a gradient magnetic field, and a gradient magnetic field controller which controls the gradient magnetic field generated by the gradient coil. The image processor may acquire the data set by arranging digital data acquired by oversampling the MR signal in the k-space based on the gradient magnetic field.

The gradient magnetic field controller may modulate the gradient magnetic field generated by the gradient coil, and the image processor may acquire the data set having the oscillated sampling pattern by arranging digital data acquired by oversampling the MR signal in the k-space based on the modulated gradient magnetic field.

The image processor may acquire the MR image based on the plurality of sub-data sets via parallel imaging.

The image processor may acquire the MR image via Sensitivity encoding (SENSE) or Generalized Auto-calibrating Partially Parallel Acquisition (GRAPPA).

The image processor may oversample the MR signal at a sampling rate that is higher than a Nyquist rate that is determined based on an FOV of the MR image.

According to one or more embodiments, an MR imaging method includes acquiring an MR signal received by at least one channel coil; acquiring a data set of a k-space for the at least one channel coil by oversampling the MR signal in a readout direction of the k-space; dividing the data set into a plurality of sub-data sets; and acquiring an MR image based on the plurality of sub-data sets.

[Mode for Invention]

This application claims the benefit of Korean Patent Application No. 10-2014-0151218, filed on Nov. 3, 2014, in the Korean Intellectual Property Office, the disclosure of which is incorporated herein in its entirety by reference.

Additional aspects will be set forth in part in the description which follows and, in part, will be apparent from the description, or may be learned by practice of the presented embodiments.

The attached drawings for illustrating exemplary embodiments of the present disclosure are referred to in order to gain a sufficient understanding of the present disclosure, the merits thereof, and the objectives accomplished by the implementation of the present disclosure. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present disclosure will only be defined by the appended claims.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present disclosure means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In the following description, well-known functions or constructions are not described in detail so as not to obscure the embodiments with unnecessary detail.

Throughout the specification, an "image" may denote multi-dimensional data composed of discrete image elements (for example, pixels in a two-dimensional image and voxels in a three-dimensional image). For example, the image may be a medical image of an object captured by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. Furthermore, the "object" may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. Furthermore, in the present specification, a "pulse sequence" refers to continuity of signals repeatedly applied by an MRI apparatus.

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

An MRI system is an apparatus for acquiring a sectional image of a part of an object by expressing, in a contrast comparison, a strength of a MR signal with respect to a radio frequency (RF) signal generated in a magnetic field having a specific strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and acquire an MR image. The MR signal denotes an RF signal emitted from the object. An intensity of the MR signal may be determined according to a density of a predetermined atom (for example, hydrogen) of the object, a relaxation time T1, a relaxation time T2, and a flow of blood or the like.

MRI systems include characteristics different from those of other imaging apparatuses. Unlike imaging apparatuses such as CT apparatuses that acquire images according to a direction of detection hardware, MRI systems may acquire 2D images or 3D volume images that are oriented toward an optional point. MRI systems do not expose objects or examiners to radiation, unlike CT apparatuses, X-ray apparatuses, position emission tomography (PET) apparatuses, and single photon emission CT (SPECT) apparatuses, may acquire images having high soft tissue contrast, and may acquire neurological images, intravascular images, musculoskeletal images, and oncologic images that are required to precisely capturing abnormal tissues.

FIG. 1 is a block diagram of a general MRI system. Referring to FIG. 1, the general MRI system may include a gantry 20, a signal transceiver 30, a monitoring unit 40, a system control unit 50, and an operating unit 60.

The gantry 20 prevents external emission of electromagnetic waves generated by a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, in order to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Larmor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Larmor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may communicate with an external apparatus via wires and/or wirelessly, and may also perform dual tune communication according to a communication frequency band.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

The gantry 20 may further include a display 29 disposed outside the gantry 20 and a display (not shown) disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Larmor frequency to the RF coil 26, and the RF receiver 38 may receive an MR signal received by the RF coil 26.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitoring unit 40 may monitor or control the gantry 20 or devices mounted on the gantry 20. The monitoring unit 40 may include a system monitoring unit 42, an object monitoring unit 44, a table controller 46, and a display controller 48.

The system monitoring unit 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitoring unit 44 monitors a state of the object 10. In detail, the object monitoring unit 44 may include a camera for observing a movement or position of the object 10, a respiration measurer for measuring the respiration of the object 10, an electrocardiogram (ECG) measurer for measuring the electrical activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 52. For example, during moving imaging of the object 10, the table controller 46 may continuously or discontinuously move the table 28 according to the sequence control of the sequence controller 52, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system control unit 50 may include the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. Here, the pulse sequence includes all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating unit 60 may request the system control unit 50 to transmit pulse sequence information while controlling an overall operation of the MRI system.

The operating unit 60 may include an image processor 62 for receiving and processing the MR signal received by the RF receiver 38, an output unit 64, and an input unit 66.

The image processor 62 may process the MR signal received from the RF receiver 38 so as to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange digital data in a k space (for example, also referred to as a Fourier space or a frequency space) of a memory, and rearrange the digital data into image data via 2D or 3D Fourier transformation.

The image processor 62 may perform a composition process or difference calculation process on image data if required. The composition process may include an addition process on a pixel or a maximum intensity projection (MIP) process. The image processor 62 may store not only the rearranged image data but also image data on which a composition process or a difference calculation process is performed, in a memory (not shown) or an external server.

The image processor 62 may perform any of the signal processes on the MR signal in parallel. For example, the image processor 62 may perform a signal process on a plurality of MR signals received by a multi-channel RF coil in parallel so as to rearrange the plurality of MR signals into image data.

The output unit 64 may output image data generated or rearranged by the image processor 62 to the user. The output unit 64 may also output information required for the user to manipulate the MRI system, such as a user interface (UI), user information, or object information. The output unit 64 may be a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3-dimensional (3D) display, a transparent display, or any one of other various output devices that are well known to one of ordinary skill in the art.

The user may input object information, parameter information, a scan condition, a pulse sequence, or information about image composition or difference calculation by using the input unit 66. The input unit 66 may be a keyboard, a mouse, a track ball, a voice recognizer, a gesture recognizer, a touch screen, or any one of other various input devices that are well known to one of ordinary skill in the art.

The signal transceiver 30, the monitoring unit 40, the system control unit 50, and the operating unit 60 are separate components in FIG. 1, but it will be obvious to one of ordinary skill in the art that respective functions of the signal transceiver 30, the monitoring unit 40, the system control unit 50, and the operating unit 60 may be performed by another component. For example, the image processor 62 converts the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitoring unit 40, the system control unit 50, and the operating unit 60 may be connected to each other by wire or wirelessly, and when they are connected wirelessly, the MRI system may further include an apparatus (not shown) for synchronizing clock signals therebetween. Communication between the gantry 20, the RF coil 26, the signal transceiver 30, the monitoring unit 40, the system control unit 50, and the operating unit 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), optical communication, or any of other various communication methods that are well known to one of ordinary skill in the art.

FIG. 2 is a block diagram of a communicator 70 according to an embodiment of the present disclosure. Referring to FIG. 2, the communicator 70 may be connected to at least one selected from the gantry 20, the signal transceiver 30, the monitoring unit 40, the system control unit 50, and the operating unit 60 of FIG. 1.

The communicator 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 2, the communicator 70 may be connected to a network 80 by wire or wirelessly to communicate with a server 92, a medical apparatus 94, or a portable device 96.

In detail, the communicator 70 may transmit and receive data related to the diagnosis of an object through the network 80, and may also transmit and receive a medical image captured by the medical apparatus 94, such as a CT apparatus, an MRI apparatus, or an X-ray apparatus. In addition, the communicator 70 may receive a diagnosis history or a treatment schedule of the object from the server 92 and use the same to diagnose the object. The communicator 70 may perform data communication not only with the server 92 or the medical apparatus 94 in a hospital, but also with the portable device 96, such as a mobile phone, a personal digital assistant (PDA), or a laptop of a doctor or patient.

Also, the communicator 70 may transmit information about a malfunction of the MRI system or about a medical image quality to a user through the network 80, and receive a feedback regarding the information from the user.

The communicator 70 may include at least one component enabling communication with an external apparatus.

For example, the communicator 70 may include a local area communication element 72, a wired communication element 74, and a wireless communication element 76. The local area communication element 72 refers to an element for performing local area communication with an apparatus within a predetermined distance. Examples of local area communication technology according to an embodiment of the present disclosure include, but are not limited to, a wireless local area network (LAN), Wi-Fi, Bluetooth, Zig-Bee, Wi-Fi direct (WFD), ultra wideband (UWB), infrared data association (IrDA), Bluetooth low energy (BLE), and near field communication (NFC).

The wired communication element 74 refers to a element for performing communication by using an electric signal or an optical signal. Examples of wired communication technology according to an embodiment of the present disclosure include wired communication techniques using a pair cable, a coaxial cable, and an optical fiber cable, and other well known wired communication techniques.

The wireless communication element 76 transmits and receives a wireless signal to and from at least one selected from a base station, an external apparatus, and a server in a mobile communication network. Here, the wireless signal may be a voice call signal, a video call signal, or data in any one of various formats according to transmission and reception of a text/multimedia message.

FIG. 3 illustrates a data set of k-space and a field of view (FOV) of a magnetic resonance (MR) image.

Referring to FIG. 3, k-space may be expressed in a kx-ky coordinate system, and a FOV, which is image space, may be expressed in an X-Y coordinate system. In k-space, a kx-axis direction is also referred to as a read out direction and a ky-axis direction is also referred to as a phase direction.

The data set in k-space is a set of digital data arranged in k-space. In FIG. 3, the digital data is illustrated with dots. The data set in k-space may be obtained by arranging, in k-space, samples, which are digital data, acquired by sampling an MR signal, which is an analog signal. A position of digital data illustrated with dots in k-space may be expressed by (kx, ky). For example, a position of digital data at the center of the k-space may be expressed by (0, 0).

A FOV includes a plurality of pixels PX in a matrix. A resolution may be defined by the number of pixels or a size of a matrix of pixels in a FOV. Thus, a size of pixels in a FOV may vary according to resolution. A resolution of a FOV in FIG. 3 is 5×5. Each pixel PX of a FOV may correspond to a pixel value, and as each pixel expresses its pixel value, an MR image may be displayed in the FOV. The pixel value may be brightness and/or color information. Pixel values of pixels denote image data, and image data may be obtained by performing Fourier transformation (FT) on digital data in k-space.

Sampling distance dkx and dky in k-space are inversely proportional to FOV sizes FOVx and FOVy. In k-space, the number Nx of samples arranged in the readout direction kx and the number Ny of samples arranged in the phase direction ky are related with the resolution of the FOV. For example, if the number Nx of samples and the number Ny of samples increase, the number of pixels in a FOV increases and a pixel size is reduced. The smaller a pixel size, the clearer may be an MR image. Although the sample numbers Nx and Ny in the read out direction kx and the phase direction ky are each five in FIG. 3, FIG. 3 is merely exemplary.

A pattern in which digital data is arranged in k-space is referred to as a sampling pattern. In the data set of FIG. 3, all digital data are acquired in the readout direction kx at intervals of the sampling distance dkx that is based on the FOV size FOVx in the X axis. In other words, acquiring all digital data in the read out direction kx is referred to as full sampling in the read out direction kx. In the data set of FIG. 3, all digital data are acquired in the phase direction ky at intervals of the sampling distance dky that is based on the FOV size FOVy in the Y axis. In other words, acquiring all digital data in the phase direction ky is referred to as full sampling in the phase direction ky.

The gradient coil 24 of FIG. 1 may generate a gradient magnetic field at intervals of a repetition time TR. The gradient coil 24 may generate gradient magnetic fields in X-, Y-, and Z-axis directions crossing each other at right angles, at intervals of the repetition time TR. The gradient magnetic field in the Z-axis direction may be a slice gradient magnetic field that determines a cross-section of the object 10 of FIG. 1. The gradient magnetic field in the Y-axis direction may be a phase gradient magnetic field that determines a location in the phase direction ky in the k-space. The gradient coil 24 generates a phase gradient magnetic field corresponding to a location in the phase direction ky at intervals of the repetition time TR. In other words, a phase gradient magnetic field differs at each row of the k-space. The gradient magnetic field in the X-axis direction may be a readout gradient magnetic field that is applied while an MR signal is being received. Digital data acquired by sampling an MR signal that is received during the repetition time TR is arranged in a row of the k-space, and the row corresponds to the phase gradient magnetic field that is applied during the repetition time TR. In other words, digital data included in each row of the k-space may be acquired during each repetition time TR. Hereinafter, each row of the k-space is referred to as a sample line.

However, when the data set of k-space is acquired via full sampling as illustrated in FIG. 3, the time taken to obtain data increases, and thus an error may be caused in an MR image due to movement of the object 10 (see FIG. 1).

FIG. 4 is a block diagram of an MRI system 1000 including an MRI apparatus 100, according to an embodiment.

Referring to FIG. 4, the MRI system 1000 may include the MRI apparatus 100 and a gantry 200. The MRI apparatus 100 includes an RF receiver 110 and an image processor 120. The gantry 200 includes an RF coil 210. The RF coil 210 includes at least one channel coil, namely, first through M-th channel coils 210-1, 210-2, through to 210-M (where M is a natural number).

The MRI apparatus 100 and the gantry 200 may be connected to each other by wires or wirelessly. Although the MRI apparatus 100 is separated from the gantry 200 in FIG. 4, embodiments are not limited thereto. The MRI apparatus 100 may be included in the gantry 200 or integrally formed with the gantry 200.

The MRI system 1000 may be an MRI system as illustrated in FIG. 1 or a modification of the MRI system of FIG. 1 according to an embodiment. Thus, the RF receiver 110 and the image processor 120 of the MRI apparatus 100 may correspond to the RF receiver 38 and the image processor 62 of FIG. 1, respectively. The gantry 200 and the RF coil 210 may correspond to the gantry 20 and the RF coil 26 of FIG. 1, respectively. Accordingly, although not mentioned individually, the above description may be applied to several components included in the MRI system 1000 of FIG. 4.

The first through M-th channel coils 210-1, 210-2, through to 210-M of the gantry 200 receive an MR signal emitted from an object. Each of the first through M-th channel coils 210-1, 210-2, through to 210-M may receive the MR signal emitted from the object. Different MR signals may be received by the first through M-th channel coils 210-1, 210-2, through to 210-M according to position relationships between the object and the first through M-th channel coils 210-1, 210-2, through to 210-M. The RF coil 210 may transmit the received MR signals to the RF receiver 110.

The RF receiver 110 acquires the MR signals respectively received by the first through M-th channel coils 210-1, 210-2, through to 210-M.

The image processor 120 acquires data sets of k-space for the first through M-th channel coils 210-1, 210-2, through to 210-M by oversampling the MR signals. Since the MR signals may be respectively received by the first through M-th channel coils 210-1, 210-2, through to 210-M, the image processor 120 may acquire a data set of k-space for each of the first through M-th channel coils 210-1, 210-2, through to 210-M. The image processor 120 divides each of the data sets into a plurality of sub-data sets and acquires an MR image based on the plurality of sub-data sets. The operation of the image processor 120 will be described in detail later.

FIG. 5 illustrates an RF coil 310 included in an MRI system according to an embodiment. The RF coil 310 of FIG. 5 may be an example of the RF coil 210 of FIG. 4.

Referring to FIG. 5, the RF coil 310 includes a plurality of channel coils 310-1 through 310-8. The plurality of channel coils 310-1 through 310-8 may be arranged to form a cylinder. Although the RF coil 310 includes the eight channel coils 310-1 through 310-8 in FIG. 5, the number of channel coils included in the RF coil 310 is not limited to 8.

Each of the plurality of channel coils 310-1 through 310-8 may receive an MR signal emitted from an object 10. The MR signals respectively received by the plurality of channel coils 310-1 through 310-8 may be different according to position relationships between the object 10 and the plurality of channel coils 310-1 through 310-8, namely, distances, orientations, or the like between the plurality of channel coils 310-1 through 310-8 and the object 10. Sensitivity of each of the plurality of channel coils 310-1 through 310-8 may be determined according to a position relationship between the object 10 and each of the plurality of channel coils 310-1 through 310-8 and information about a signal area of the object 10 where an MR signal is generated. The sensitivity of a channel coil is a receiving sensitivity of the channel coil.

The RF coil 310 may transmit the received MR signals to the RF receiver 110 of FIG. 4. Accordingly, the RF receiver 110 of FIG. 4 may acquire the MR signals respectively received by the channel coils 310-1 through 310-8.

The image processor 120 of FIG. 4 acquires data sets of k-space for the channel coils 310-1 through 310-8 by oversampling the MR signals.

FIGS. 6A and 6B illustrate data sets of k-space. FIG. 6A is an example of a non-oversampled data set, and FIG. 6B is an example of an oversampled data set.

Referring to FIG. 6A, the data set in k-space has been full-sampled in the readout direction kx and has been undersampled in the phase direction ky. Some digital data are not acquired in the phase direction ky of the data set. There are missing lines ML from which no digital data is obtained, from among sampling lines in the k-space.

The repetition time TR is taken to acquire digital data included in a sample line. When undersampling is performed in the phase direction ky, the repetition time TR is not required to acquire a missing line ML, and thus the time taken to photograph an object may be reduced. A sampling distance 2dky in the phase direction ky of the data set of FIG. 6A is twice the sampling distance dky of the data set of FIG. 3. Accordingly, only about half data may be acquired in the phase direction ky in the data set of FIG. 6A compared to the data set of FIG. 3. Therefore, the photographing time taken to acquire the data set of FIG. 6A may be reduced to half the photographing time taken to acquire the data set of FIG. 3. In other words, an acceleration factor of the data set of FIG. 6A is 2.

Referring to FIG. 6B, the data set in k-space has been oversampled in the readout direction kx and has been undersampled in the phase direction ky. A sampling distance ½dkx in the readout direction kx of the data set of FIG. 6B is a half of the sampling distance dkx of the data set of FIG. 6A. Accordingly, about twice data may be acquired in the readout direction kx in the data set of FIG. 6B compared to the data set of FIG. 6A. A sampling distance 2dky in the phase direction ky of the data set of FIG. 6B is equal to the sampling distance 2dky of the data set of FIG. 6A. In FIG. 6B, digital data included in each sample line of the k-space may be acquired by oversampling an MR signal at intervals of the repetition time TR. In other words, to acquire oversampled digital data included in a single sample line of FIG. 6B, the repetition time TR is taken as illustrated in FIG. 6A. In other words, the time taken to acquire the data set of FIG. 6B does not increase compared with FIG. 6A. Accordingly, an acceleration factor of the data set of FIG. 6B is 2 as in FIG. 6A.

Oversampling in the readout direction kx denotes sampling an MR signal at a rate that is higher than a Nyquist rate. The Nyquist rate may be determined based on the FOV of an MR image. In particular, the Nyquist rate may be determined based on an X-axis size of the FOV (i.e., the FOV size FOVx of FIG. 3). The Nyquist rate is a sampling rate in the readout direction kx, and may be determined to be a sampling rate that satisfies the FOV in the readout direction kx in consideration of the size of a readout gradient magnetic field.

Referring back to FIG. 4, the image processor 120 acquires a data set of k-space for at least one channel coil by oversampling an MR signal. For example, the image processor 120 may acquire the data set of FIG. 6B. The image processor 120 may divide the data set into a plurality of sub-data sets. In other words, the image processor 120 may reorganize the data set into a plurality of independent sub-data sets.

FIG. 7 illustrates an example in which an MRI apparatus according to an embodiment divides a data set acquired via oversampling into a plurality of sub-data sets. The example of FIG. 7 may be performed by the image processor 120 of FIG. 4.

Referring to FIG. 7, the image processor 120 may acquire a data set DSm of k-space for an m-th channel coil from among a plurality of channel coils via oversampling, wherein m is a natural number. The data set DSm may be raw data generated in k-space. A sampling pattern of the data set DSm of FIG. 7 is the same as the sampling pattern of the data set of FIG. 6B. The m-th channel coil may be one of the plurality of channel coils (e.g., the first through M-th channel coils 210-1 through 210-M of FIG. 4). The image processor 120 may acquire the data set DSm (m=1, 2, . . . , or M) of the k-space for each of the plurality of channel coils (e.g., the first through M-th channel coils 210-1 through 210-M of FIG. 4).

The image processor 120 may divide the data set DSm of k-space acquired via oversampling into a plurality of sub-data sets, for example, a first sub-data set SDm1 and a second sub-data set SDm2. The image processor 120 may divide the data set DSm such that neighboring pieces of digital data in the readout direction kx in the data set DSm are included in different sub-data sets.

Since about twice data is acquired in the data set DSm of FIG. 7 in the readout direction kx, the data set DSm is divided into the two sub-data sets SDm1 and SDm2. However, a data set may be divided into at least two sub-data sets according to sampling rates.

A first image Im1(x,y) may be acquired from the first sub-data set SDm1, and a second image Im2(x,y) may be acquired from the second sub-data set SDm2. In the first and second images Im1(x,y) and Im2(x,y), (x, y) indicates a location of a pixel within an image (see FIG. 3). Each of the first image Im1(x,y) and the second image Im2(x,y) may indicate a pixel value of a pixel at the location (x, y). The first image Im1(x,y) and the second image Im2(x,y) may be expressed as in Equation 1.

$$Im1(x,y)=Im(x,y)+Im(x,y-0.5\text{FOV}y)$$

$$Im2(x,y)=Im1(x,y)\exp(j\pi x/\text{FOV}x) \quad [\text{Equation 1}]$$

In Equation 1, Im(x,y) is an m-th channel coil image which is an image for an m-th channel coil when oversampling is not performed. FOVx is an x-axis size of the FOV of each image and FOVy is an x-axis size of the FOV of each image (see FIG. 3).

As such, since the data set DSm of k-space for each channel coil may extend to the first sub-data set SDm1 and the second sub-data set SDm2, data sets for M channel coils may extend to 2M sub-data sets.

The image processor may acquire an MR image based on the first and second sub-data sets SDm1 and SDm2. In other words, the image processor may acquire an MR image, based on the 2M sub-data sets into which the data sets for the M channel coils are extended. The image processor may acquire an MR image via image reconstruction. For example, the image reconstruction method may be parallel imaging, compressed sensing, or the like. Examples of the parallel imaging may include k space-based Generalized Auto-calibrating Partially Parallel Acquisition (GRAPPA) and image-based Sensitivity encoding (SENSE).

The image processor may need to accurately determine correlations among the plurality of sub-data sets in order to acquire an MR image. To this end, the image processor may acquire additional data. For example, calibration data, which is additional data, may be acquired via a calibration measurement process for measuring a location on the k-space on which data of the data set are mapped. The additional data may also be acquired when the data set is acquired. In other words, the image processor may acquire the additional data such as calibration data from a portion of the data set. Alternatively, the image processor may acquire the additional data by further photographing an object by using the MRI system 1000 of FIG. 4, independently of the data set acquiring process. In other words, the additional data may be acquired independently of the data set.

A case where an MR image is acquired via GRAPPA will be first described.

The image processor estimates missing data MD, which is not acquired in each of the 2M sub-data sets SDm1 and SDm2 (m=1, 2, . . . , or M) for the M channel coil. The image processor may acquire calibration data of each of the sub-data sets SDm1 and SDm2 via calibration. The image processor may estimates the missing data MD on missing lines ML, based on sample lines from which digital data is acquired and the calibration data in each of the sub-data sets SDm1 and SDm2.

As such, the image processor may acquire corrected 2M sub-data sets by estimating the missing data MD from each of the 2M sub-data sets SDm1 and SDm2 (m=1, 2, . . . , or M). The image processor may acquire 2M channel coil images by individually performing Fourier transformation on the corrected 2M sub-data sets. The image processor may acquire an MR image, which is a final image, by synthesizing the 2M channel coil images. The MR image obtained by synthesizing the 2M channel coil images may have an improved signal to noise ratio (SNR), compared with the case where M channel coil images are synthesized.

Next, a case where an MR image is acquired via SENSE will be described.

When the MR image, which is a final image, is I(x,y) and the sensitivity of an m-th channel coil is Cm(x,y), an m-th channel coil image Im(x,y) having no aliasing may be expressed as in Equation 2.

$$Im(x,y)=Cm(x,y)I(x,y) \quad \text{[Equation 2]}$$

The first image Im1(x,y) and the second image Im2(x,y) may be expressed as in Equation 3, which is obtained from Equation 2:

$$Im1(x,y)=Im(x,y)=Cm(x,y)I(x,y)$$

$$Im2(x,y)=Im(x,y)\exp(j\pi x/\text{FOV}x)=Cm(x,y)\exp(j\pi x/\text{FOV}x)I(x,y) \quad \text{[Equation 3]}$$

A first virtual sensitivity Cm1(x,y) and a second virtual sensitivity Cm2(x,y) may be expressed as in Equation 4, which is obtained from Equation 3:

$$Cm1(x,y)=Cm(x,y)$$

$$Cm2(x,y)=Cm(x,y)\exp(j\pi x/\text{FOV}x) \quad \text{[Equation 4]}$$

As such, when the data set DSm of k-space for each channel coil is extended into the plurality of sub-data sets SDm1 and SDm2, 2M virtual channel coil images having the first and second virtual sensitivities Cm1(x,y) and Cm2(x,y), which are different, may be obtained. The image processor may acquire the MR image, which is a final image, by synthesizing the 2M channel coil images based on a sampling pattern of the k-space and virtual sensitivity information. When the M channel coils are extended into the 2M virtual channel coils having different virtual sensitivities, the quality of an MR image acquired via SENSE may improve.

As such, by dividing a data set acquired via oversampling into a plurality of sub-data sets according to an embodiment, an MR image having an improved quality may be acquired. Oversampling at a rate that is equal to or higher than the Nyquist rate may not greatly affect an improvement in the quality of an MR image via aliasing removal, SNR improvement, or the like. However, according to some embodiments, a data set obtained via oversampling is extended into a plurality of sub-data sets, and each of the sub-data sets are processed as an independent data set, and thus parallel imaging in which all pieces of data of the data set obtained via oversampling are fully utilized may be performed. Accordingly, the quality of a reconstructed image may improve. When oversampling in a readout direction is performed, the time taken to photograph an object does not increase. Rather, the time taken to photograph an object may be shortened by increasing an acceleration factor of a data set.

FIG. 8 is a block diagram of an MRI system 2000 according to an embodiment. The MRI system 2000 of FIG. 8 may be a modification of the MRI system 1000 of FIG. 4 according to an embodiment. Accordingly, although not mentioned individually, the above description may be applied to several components included in the MRI system 2000 of FIG. 8.

Referring to FIG. 8, the MRI system 2000 may include an MRI apparatus 400 and a gantry 500. The MRI apparatus 400 may include an RF receiver 410, an image processor 420, an RF controller 430, and a gradient magnetic field controller 440. The gantry 500 may include an RF coil 510 and a gradient coil 520. The RF coil 510 includes at least one channel coil, namely, first through M-th channel coils 510-1, 510-2, through to 510-M (where M is a natural number).

The RF controller 430 may drive or control the RF coil 510. The RF coil 510 may radiate an RF signal to the object 10 under the control of the RF controller 430. The gradient magnetic field controller 440 may drive or control the gradient coil 520. The gradient coil 520 may generate a gradient magnetic field under the control of the gradient magnetic field controller 440. The RF coil 510 may receive an MR signal emitted from the object 10. The gradient magnetic field controller 440 may determine a gradient magnetic field that is generated by the gradient coil 520, based on sensitivity of each of the first through M-th channel coils 510-1 through 510-M and information about a signal area of the object 10 where the MR signal is generated.

The RF receiver 410 acquires MR signals respectively received by the first through M-th channel coils 510-1, 510-2, through to 510-M. The image processor 420 acquires data sets of k-space for the first through M-th channel coils 510-1, 510-2, through to 510-M by oversampling the MR signals. The image processor 420 may acquire a data set by arranging digital data acquired by oversampling an MR signal in the k-space based on the gradient magnetic field. In detail, at intervals of the repetition time TR, the RF coil 510 may radiate an RF signal to the object 10 and the gradient coil 520 may generate a gradient magnetic field. The image processor 420 may acquire digital data by oversampling the MR signal at intervals of the repetition time TR and also acquire a data set of k-space by arranging the digital data acquired during the repetition time TR on a corresponding row in the k-space.

The image processor 420 divides the data set into a plurality of sub-data sets and acquires an MR image based on the plurality of sub-data sets.

The image processor 420 may acquire a data set having a sampling pattern like the data set DSm of FIG. 7. Alternatively, the image processor 420 may acquire a data set in which a sampling pattern is oscillated in a phase direction of the k-space. A data set having an oscillated sampling pattern will now be described with reference to FIG. 9.

FIG. 9 illustrates an example of a data set of k-space that is obtained by an image processor, according to an embodiment.

Referring to FIG. 9, the data set of k-space has been oversampled in the readout direction kx and has been undersampled in the phase direction ky, and oscillation is applied in the phase direction ky. A sampling distance ½dkx in the readout direction kx of the data set of FIG. 9 and a sampling distance 2dky in the phase direction ky thereof are the same as those of the data set of FIG. 6B. In other words, an acceleration factor of the data set of FIG. 9 is 2 as in FIG. 6B. An oscillation amplitude OA for a sampling distance dky in the phase direction ky in the data set of FIG. 9 is 1. As the oscillation amplitude OA increases, the quality of an MR image may improve. As the period of the oscillation decreases, the quality of an MR image may improve.

Referring to FIGS. 8 and 9, the data set of k-space having an oscillated sampling pattern illustrated in FIG. 9 may be acquired by the gradient magnetic field controller 440 modulating the gradient magnetic field generated by the gradient coil 520. In detail, the image processor 420 may acquire the data set of k-space having an oscillated sampling pattern illustrated in FIG. 9 by arranging digital data acquired by oversampling the MR signal in k-space based on the modulated gradient magnetic field. For example, the gradient magnetic field controller 440 may modulate the gradient magnetic field generated by the gradient coil 520, at interval of the repetition time TR.

FIGS. 10A-15C illustrate results of simulations performed using a numerical phantom. FIGS. 10A, 11A, 12A, 13A, 14A, and 15A illustrate data sets in k-space, FIGS. 10B, 11B, 12B, 13B, 14B, and 15B illustrate MR images respectively obtained based on the data sets, and FIGS. 10C, 11C, 12C, 13C, 14C, and 15C illustrate error maps of the MR images. The data sets illustrated in FIGS. 10A, 11A, 12A, 13A, 14A, and 15A may be data sets in k-space that are acquired from MR signals for eight channel coils. In other words, a data set may be acquired for each channel coil. Random noise in which a bandwidth according to oversampling in a readout direction has been reflected may be added to the MR signal. The MR images illustrated in FIGS. 10B, 11B, 12B, 13B, 14B, and 15B may be MR images reconstructed via parallel imaging based on the data set for each channel coil as illustrated in FIGS. 10A, 11A, 12A, 13A, 14A, and 15A.

FIGS. 10A, 10B, and 10C illustrate a case where an MR image is acquired based on a data set of k-space that is acquired via full sampling. An acceleration factor RP in a phase direction ky of the data set of FIG. 10A is 1, and an undersampling factor RF in a readout direction kx thereof is 1. The MR image of FIG. 10B has a Normalized Root-Mean-Square Error (NRMSE) of 0.00006914. Referring to the error map of FIG. 10C, a noise aspect is uniform on a space.

FIGS. 11A, 11B, and 11C illustrate a case where an MR image is acquired based on a data set of k-space that is acquired via undersampling. An acceleration factor RP in a phase direction ky of the data set of FIG. 11A is 4, and an undersampling factor RF in a readout direction kx thereof is 1. The MR image of FIG. 11B has an NRMSE of 0.00029766. Compared with FIGS. 10A-10C, the data set of FIG. 11A may be acquired four times faster than the data set of FIG. 10A, but the NRMSE of the MR image of FIG. 11B is higher than that of the MR image of FIG. 10B. Referring to the error map of FIG. 11C, a noise aspect varies according to spaces.

FIGS. 12A-15C illustrate a case where an MR image is acquired based on a data set of k-space that has been oversampled in a readout direction and to which oscillation has been applied in a phase direction. In FIGS. 12A, 13A, 14A, and 15A, acceleration factors RP in phase directions ky of the data sets are each 4, and undersampling factors RF in readout directions kx thereof are each 0.5. In other words, oversampling has been performed in the readout directions kx in the data sets of FIGS. 12A, 13A, 14A, and 15A. In FIGS. 12A, 13A, 14A, and 15A, oscillation amplitudes OA for sampling distances in the phase directions ky of the data sets are each 2. However, cycles of oscillation in the readout directions kx of FIGS. 12A, 13A, 14A, and 15A are 16, 32, 64, and 128, respectively. In other words, in a direction from FIG. 12A to FIG. 15A, a cycle of oscillation increases by two times, and a period of oscillation decreases by ½.

The NRMSEs of FIGS. 12B, 13B, 14B, and 15B are 0.00024492, 0.00018892, 0.00015246, and 0.00014228, respectively. In other words, as the cycle of oscillation increases, a NRMSE may decrease and the quality of an MR image may increase. Referring to the error maps of FIGS. 12C, 13C, 14C, and 15C, as the cycle of oscillation increases, a noise aspect becomes more uniform according to spaces. In other words, as the cycle of oscillation increases, the uniformity of noise increases and a NRMSE decreases, and thus the quality of an MR image may increase.

The NRMSEs of FIGS. 12B, 13B, 14B, and 15B are between the NRMSE of FIG. 11B and the NRMSE of FIG. 10B. In other words, the quality of an MR image based on an oversampled data set of k-space to which oscillation has been applied improves compared with that based on an undersampled data set as in FIG. 11A-11C. In particular, as the cycle of oscillation increases, the quality of an image may further improve. Although the NRMSEs of FIGS. 12B, 13B, 14B, and 15B are larger than the NRMSE of FIG. 10B, the data sets of k-space of FIGS. 12A, 13A, 14A, and 15A are acquired 4 times faster than in the case of FIGS. 10A-10C.

In particular, in the case of FIGS. 15A-15C providing a maximum cycle of oscillation, from among the cases of FIGS. 12A-12C through FIGS. 15A-15C, the NRMSE is about twice that of the case of FIGS. 10A-10C and thus the SNR is about a half of that of the case of FIGS. 10A-10C. However, the NRMSE of the data set of FIGS. 15A-15C may be about a half of that of the undersampled data set of FIGS. 11A-11C, and thus the SNR in the case of FIGS. 15A-15C may greatly improve compared with the case of FIGS. 11A-11C. In the case of FIGS. 15A-15C, no structured aliasing occurs.

FIG. 16 is a flowchart of an MR imaging method according to an embodiment.

Referring to FIG. 16, an MR signal received by at least one channel coil is acquired, in operation S110. The MR signal may be acquired for each of the at least one channel coil. In operation S120, a data set of k-space for the at least one channel coil is acquired by oversampling the MR signal. In this case, the MR signal may be oversampled in a readout direction of the k-space. Oversampling may denote sampling the MR signal at a sampling rate that is higher than the Nyquist rate. The MR signal may be undersampled in a phase direction of the k-space. The data set may have an oscillated sampling pattern in the phase direction of the k-space. The oscillated sampling pattern may be acquired by modulating a gradient magnetic field generated by a gradient coil. In detail, the data set having the oscillated sampling pattern may be acquired by arranging digital data acquired by oversampling the MR signal in k-space based on the modulated gradient magnetic field.

In operation S130, the data set may be divided into a plurality of sub-data sets. In operation S140, an MR image is acquired based on the plurality of sub-data sets. The MR image may be acquired based on the plurality of sub-data sets, via parallel imaging. Examples of the parallel imaging include SENSE and GRAPPA.

The MRI processing method of FIG. 16 may be performed in an MRI apparatus or an MRI system according to the one or more of the above embodiments of the present disclosure. Each operation of the MR imaging method may be performed according to the above-described manner.

The embodiments of the present disclosure can be written as computer programs and can be implemented in general-use digital computers that execute the programs using a computer readable recording medium.

Examples of the computer readable recording medium include magnetic storage media (e.g., ROM, floppy disks, hard disks, etc.), optical recording media (e.g., CD-ROMs, or DVDs), etc.

The exemplary embodiments should be considered in descriptive sense only and not for purposes of limitation. Descriptions of features or aspects within each embodiment should typically be considered as available for other similar features or aspects in other embodiments.

While the present disclosure has been particularly shown and described with reference to exemplary embodiments thereof, it will be understood by those of ordinary skill in the art that various changes in form and details may be made therein without departing from the spirit and scope as defined by the following claims.

The invention claimed is:

1. A magnetic resonance imaging (MRI) apparatus comprising:
a radio frequency (RF) receiver which acquires a magnetic resonance (MR) signal received by at least one channel coil; and
an image processor which acquires a data set of a k-space, which is formed by a first axis corresponding to a readout direction of the k-space and a second axis corresponding to a phase direction of the k-space, for the at least one channel coil by oversampling the MR signal in the readout direction of the k-space, divides the data set into a plurality of sub-data sets, and acquires an MR image based on the plurality of sub-data sets, and
wherein a sampling rate in the readout direction is greater than a sampling rate in the phase direction.

2. The MRI apparatus of claim 1, wherein the image processor undersamples the MR signal in a phase direction of the k-space.

3. The MRI apparatus of claim 2, wherein the image processor acquires the MR image based on the plurality of sub-data sets via parallel imaging.

4. The MRI apparatus of claim 3, wherein the image processor acquires a plurality of channel coil images for a plurality of virtual channel coils respectively having virtual sensitivities, based on the plurality of sub-data sets, and acquires the MR image by synthesizing the plurality of channel coil images based on a sampling pattern of the k-space and the virtual sensitivities.

5. The MRI apparatus of claim 3, wherein the image processor acquires a plurality of corrected sub-data sets by estimating missing data that is data not acquired in each of the plurality of sub-data sets, and acquires the MR image based on the plurality of corrected sub-data sets.

6. The MRI apparatus of claim 5, wherein the image processor estimates the missing data in each of the plurality of sub-data sets, based on calibration data that is acquired via calibration.

7. The MRI apparatus of claim 6, wherein the image processor acquires the calibration data from a portion of the data set or acquires the calibration data independently of the data set.

8. The MRI apparatus of claim 1, wherein the image processor oversamples the MR signal at a sampling rate that is higher than a Nyquist rate that is determined based on a field of view (FOV) of the MR image.

9. The MRI apparatus of claim 1, wherein the data set acquired by the image processor includes an oscillated sampling pattern in a phase direction of the k-space.

10. The MRI apparatus of claim 9, further comprising a gradient coil controller which modulates a gradient magnetic field that is generated by a gradient coil,
wherein the image processor acquires the data set having the oscillated sampling pattern by arranging digital data acquired by oversampling the MR signal in the k-space based on the modulated gradient magnetic field.

11. A magnetic resonance imaging (MRI) system comprising:
at least one radio frequency (RF) channel coil which receives a magnetic resonance (MR) signal emitted from an object;
an RF receiver which acquires the MR signal; and
an image processor which acquires a data set of a k-space, which is formed by a first axis corresponding to a readout direction of the k-space and a second axis corresponding to a phase direction of the k-space, for the at least one RF channel coil by oversampling the MR signal in the readout direction of the k-space, divides the data set into a plurality of sub-data sets, and acquires an MR image based on the plurality of sub-data sets, and
wherein a sampling rate in the readout direction is greater than a sampling rate in the phase direction.

12. The MRI system of claim 11, wherein the image processor undersamples the MR signal in a phase direction of the k-space.

13. The MRI system of claim 12, further comprising:
a gradient coil which generates a gradient magnetic field; and
a gradient magnetic field controller which controls the gradient magnetic field generated by the gradient coil,
wherein the image processor acquires the data set by arranging digital data acquired by oversampling the MR signal in the k-space based on the gradient magnetic field.

14. The MRI system of claim 13, wherein
the gradient magnetic field controller modulates the gradient magnetic field generated by the gradient coil, and
the image processor acquires a data set having an oscillated sampling pattern by arranging digital data acquired by oversampling the MR signal in the k-space based on the modulated gradient magnetic field.

15. The MRI system of claim 14, wherein the image processor acquires the MR image based on the plurality of sub-data sets via parallel imaging.

16. The MRI system of claim 15, wherein the image processor acquires the MR image via Sensitivity encoding (SENSE) or Generalized Auto-calibrating Partially Parallel Acquisition (GRAPPA).

17. The MRI system of claim 12, wherein the image processor oversamples the MR signal at a sampling rate that is higher than a Nyquist rate that is determined based on a field of view (FOV) of the MR image.

18. A magnetic resonance (MR) imaging method comprising:
acquiring a magnetic resonance (MR) signal received by at least one channel coil;
acquiring a data set of a k-space, which is formed by a first axis corresponding to a readout direction of the k-space and a second axis corresponding to a phase direction of the k-space, for the at least one channel coil by oversampling the MR signal in the readout direction of the k-space;
dividing the data set into a plurality of sub-data sets; and
acquiring an MR image based on the plurality of sub-data sets,
wherein a sampling rate in the readout direction is greater than a sampling rate in the phase direction.

19. The method of claim 18, wherein the data set includes an oscillated sampling pattern in a phase direction of the k-space.

20. A non-transitory computer-readable recording medium having recorded thereon a program for executing the MR imaging method of claim 18.

* * * * *